United States Patent [19]

Gau et al.

[11] Patent Number: 4,484,468
[45] Date of Patent: Nov. 27, 1984

[54] AUTOMATIC VISCOMETER

[75] Inventors: Gerald S. Gau; Vladimir Vaynshteyn, both of Houston, Tex.

[73] Assignee: Halliburton Company, Duncan, Okla.

[21] Appl. No.: 412,341

[22] Filed: Aug. 27, 1982

[51] Int. Cl.³ ............................................. G01N 11/14
[52] U.S. Cl. .......................................... 73/60; 364/509
[58] Field of Search ...................... 73/59, 60; 364/509, 364/510

[56] References Cited

U.S. PATENT DOCUMENTS

| | | | |
|---|---|---|---|
| 3,875,791 | 4/1975 | Fitzgerald et al. | 73/59 |
| 4,062,225 | 12/1977 | Murphy, Jr. et al. | 73/60 |
| 4,299,118 | 11/1981 | Gau et al. | 73/59 |
| 4,299,119 | 11/1981 | Fitzgerald et al. | 73/59 |
| 4,352,287 | 10/1982 | Orth et al. | 73/60 |

*Primary Examiner*—Gerald Goldberg
*Assistant Examiner*—Joseph W. Roskos
*Attorney, Agent, or Firm*—William J. Beard

[57] ABSTRACT

An improved rotational viscometer for testing drilling muds is disclosed. In a preferred and illustrated embodiment, a rotatable tubular sleeve is driven by a pulsed stepper motor. The drilling mud couples to a bob of cylindrical shape supported on a shaft. The sleeve is rotated or torqued, applying rotation to the shaft which is monitored by an optical encoder. The stepper motor is driven for a programmable sequence of specific intervals at specific speeds, and the mud coupled rotation at the encoder shaft is observed. The data obtained is scaled to provide an indication of viscosity and other measurements of the drilling mud indicated by an output LED display or other display type as desired. The mud is tested by a specified sequence of test procedures sanctioned by the American Petroleum Institute.

17 Claims, 3 Drawing Figures

AUTOMATIC VISCOMETER

BACKGROUND OF THE DISCLOSURE

The disclosure below sets forth a viscometer which is particularly adapted to measure characteristics of drilling fluid, commonly known as drilling mud. It is a device which is aptly made portable so that it can be used in field locations including remotely located drilling rigs. It carries out a routine in testing for viscosity. The apparatus disclosed herein is an improvement over the structure shown in U.S. Pat. No. 4,299,118 which is assigned to the common assignee of this disclosure. The reference discloses what might be termed a motor drive system using circuitry quite different from the control circuitry and power mechanism set forth in this disclosure.

This disclosure incorporates a pulsed stepper motor. For instance, the TRW Company provides a stepper motor which is sold under the trademark GLOBE. Two hundred voltage pulses are required to rotate this motor one full revolution in the full step mode. There are other brands of pulsed motors which have larger increments of rotation. Whatever the choice of pulsed motors, it is driven by voltage pulses. The pulses are applied in relatively rapid fashion so that it turns smoothly. Smoothing is also obtained through the utilization of first and second flywheels, one being on the pulse motor and the other being a relatively larger pulley for rotating a tubular sleeve. The two are connected together by an elastomeric belt. The belt and relatively heavy flywheels smooth rotation so that the rotating sleeve is observed to rotate smoothly, not jerkily. This stirs and mixes drilling mud smoothly. The use of a pulse motor enables the use of digital drive circuitry. This eliminates feedback circuits for motor speed control. Rather, the position of the rotating tubular sleeve in the drilling fluid is known because the pulse motor faithfully follows the pulses applied to it to carry out the test program. A stored program is placed in a memory, the apparatus preferably having a microprocessor along with "read only memory" and "random access memory" (ROM and RAM hereinafter), thereby enabling the stored program to drive the system. If need be, the stored program can be changed.

The present apparatus further utilizes a shaft which is connected to a non-metallic plumb bob which is submerged in the mud undergoing test. The bob is connected to a support shaft. The upper end of the support shaft connects with a coiled spring which returns the bob to a reference azimuth. The shaft is rotationally connected to a rotational encoder. Its deflection is measured dynamically against a reference azimuth. The rotating tubular sleeve (immersed in the fluid undergoing tests) thus couples torque through the mud or drilling fluid to the bob concentric within the tubular sleeve.

Consider the following test sequence exemplary of the present apparatus in operation utilizing a stored program for carrying out the test described below. After filling a container with the drilling fluid undergoing tests and placing it where the bob is completely submerged, and further submerging the tubular sleeve to a specified depth, the following routine is carried out. First of all, with everything stationary, initial movement is begun with a ramp. The rotational velocity of the tubular sleeve is ramped up to 900 RPM. This speed is held for a specified time interval. Thereafter, it is ramped down to another speed, typically 600 RPM. These two velocities are derived from drilling mud specifications published by the American Petroleum Institute (API). On reaching 600 RPM, the first step in processing of obtained data occurs. Rotation of the bob from the zero or reference azimuth is measured. Rotation of the bob occurs as the speed stabilizes within the same defined limits at 600 RPM. The angular displacement of the bob is sensed from the zero azimuth position and continues to be sensed until it stabilizes.

The motor is driven through a second sequence, namely its speed is ramped down from 600 RPM to 300 RPM. The plumb bob changes its angular position as the sleeve speed slows down. Operation is continued at 300 RPM under program control until the bob azimuth angle has stabilized within some defined limit. The tubular sleeve is then stopped for 10 seconds following the API testing standard.

After the 10 second stop, the motor is run at 3 RPM and the peak angular deflection of the bob is observed as an indication of the gel strength of the drilling fluid. Following this, the motor is again ramped up to 900 RPM for 10 seconds of mixing following the API test standard. The motor is then stopped for a waiting interval of 10 minutes according to the API test standard. After the 10 minute wait, the motor is again run at 3 RPM and the peak bob displacement is again observed as an indication of the gel strength of the drilling fluid. The API test sequence is then completed for this fluid sample. The sequence may be repeated for the same sample as desired or a new sequence begun on a new sample at this point.

The microprocessor in the apparatus has thus measured and stored data which is indicative of the bob angular displacement from reference azimuth at 600 RPM and a separate but similar measurement at 300 RPM. Additional bob peak angular displacements have been obtained after specific shutdown intervals, these being preferably 10 seconds and 10 minutes (per API standards) to provide gel strength measurements. The microprocessor displays the aforedescribed data scaled and adjusted by stored scale factors to indicate measurements of viscosity. As desired, the data can be output onto hard copy or stored in memory.

The foregoing describes the nature of the present apparatus which is briefly summarized as a concentrically arranged bob (a solid cylindrical mass) on a shaft surrounded by a rotating sleeve. The two are dipped into the drilling fluid undergoing test to a specified depth stored in a container. A pulse motor drives the rotating sleeve. The motor in turn is driven by a pulsing circuit gated at specified rates by means of a stored sequence of instructions in Read Only Memory (ROM), and the measurements obtained from the rotatable bob as observed by an optical encoder are available for visual output through a LED display, or in memory, or to a suitably interfaced hard copy output device.

BRIEF DESCRIPTION OF THE DRAWINGS

So that the manner in which the above recited features, advantages and objects of the invention, as well as others, which will become apparent, are attained and can be understood in detail, a more particular description of the invention, briefly summarized above, may be had by reference to the embodiments thereof illustrated in the appended drawings, which drawings form a part of this specification. It is to be noted, however, that the appended drawings illustrated only typical embodiments of the invention and are not to be considered limiting of its scope, for the invention may admit to other equally effective embodiments.

DETAILED DESCRIPTION OF THE PREFERRED EMBODIMENT

Figure 1:
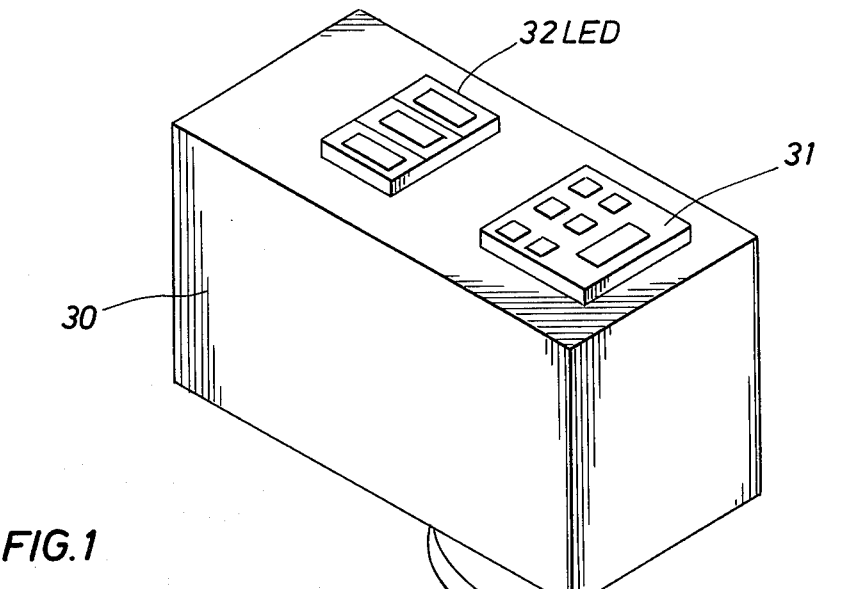
FIG. 1 is a perspective view of the viscosity measuring apparatus of the present invention showing an arrangement of stepper motor and tubular sleeve concentric about a non-metalic bob on a deflectable shaft.
Figure 1:
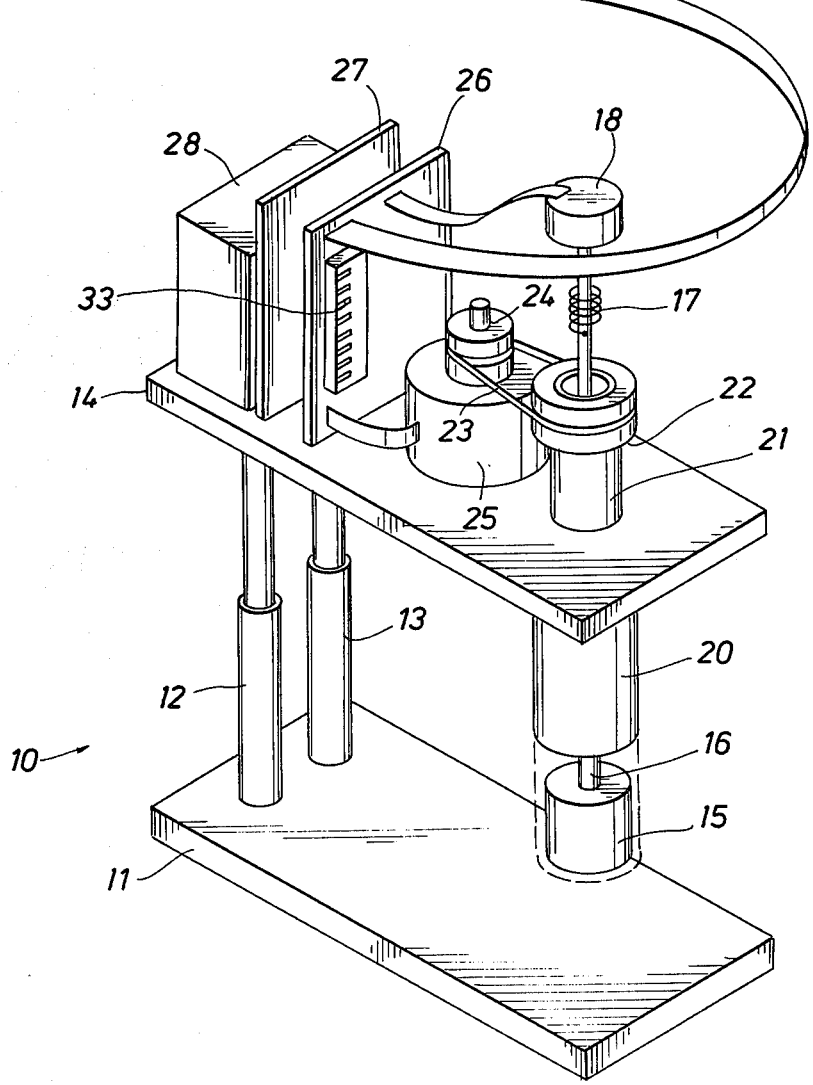

Attention is first directed to FIG. 1 of the drawings which shows the apparatus of the present invention. The numeral 10 identifies the viscosity measuring apparatus. It comprises a bottom or base 11 which supports upstanding legs 12 and 13. They extend upright to a component platform 14 is parallel to the base. It is spaced above the base by a distance sufficient to enable a container of drilling fluid, or drilling mud as it is sometimes known, to be placed on the base. The container is filled to a specified depth. Preferably, it is filled so that it completely covers over a non-metallic rotatable bob 15. The bob 15 is supported on a shaft 16. The shaft rotates through a specified angle against a torsion spring 17. The spring 17 is connected to the shaft to resist its rotation. One end of the coil spring is connected to the shaft while the other end is connected to a fixed cabinet or housing around the apparatus. The cabinet or housing has been broken away for sake of clarity. The shaft 16 also connects with an optical encoder 18 which forms a signal indicative of rotation of the shaft 16. In the quiescent state, the shaft has a rest angular position relative at a particular azimuth, and that will be referred to as the reference azimuth. A pointer painted on the bob 15 can identify the reference azimuth. During testing, the non-metallic bob is rotated through an angle which is encoded by the encoder 18 and forms an output for use in the viscosity testing of drilling fluids.

The non-metallic bob operates as a sensor. It senses the rotation of the fluid which is coupled to the fluid from a tubular sleeve 20. The tubular sleeve 20 is a hollow cylindrical sleeve. It is larger in diameter and therefore able to fit over the non-metallic bob. Clearances between the bob and the sleeve 20 are specified. The physical dimensions of the bob 15 and the sleeve 20 are also specified. The bob preferably is formed of a non-metallic material such as polyvinyl chloride. This reduces the specific heat and thermal conductivity of the bob in contrast with metals such as brass or stainless steel. This avoids altering the thermal balance of the fluid undergoing test wherein the bob is not a large heat sink. Moreover, this provides a surface which is not corrosive and which dose not stain or otherwise age with use. The sleeve 20 is formed of a selected material which does not stain or age with use. Its surface is smooth. The same is also true of the bob.

The sleeve 20 is supported by suitable pillow blocks, bearing assemblies and alignment shims (not shown) beneath the platform 14. The sleeve 20 is concentric with the shaft 16. The sleeve connects with a hollow rotatable shaft 21 which is above the platform 14. It supports a large pulley 22 which is journalled to it. The pulley 22 engages a drive belt 23 which in turn wraps around a smaller pulley 24. That is the drive pulley which is powered by a stepping motor 25 supported on the platform 14. The belt 23 is preferably an elastomeric belt of typical construction received in slightly dished circular grooves in the pulleys 22 and 24. The pulley 22 is relatively heavy to provide a flywheel effect. The sleeve is rotated smoothly because jerks resulting from pulsation of the motor 25 are smoothed by elongation, albeit small, of the elastomeric belt 23. The belt is sized to provide acceptable tension in the belt between the two pulleys which are on spaced axes of rotation. The motor 25 is a stepping motor which is driven by suitable pulse amplifiers supported on a printed circuit board 26 which is upstanding from the platform 14. Suitable additional printed circuit boards are shown at 27, and a battery assembly 28 is also supported on the platform 14. A cover or housing 30 passes over the equipment shown in FIG. 1. A suitable key pad array for entry of instructions is incorporated at 31, and an LED display is also incorporated at 32. The cover 30 is placed on the platform 14 to enclose the apparatus shown in FIG. 1 covered.

Figure 2:
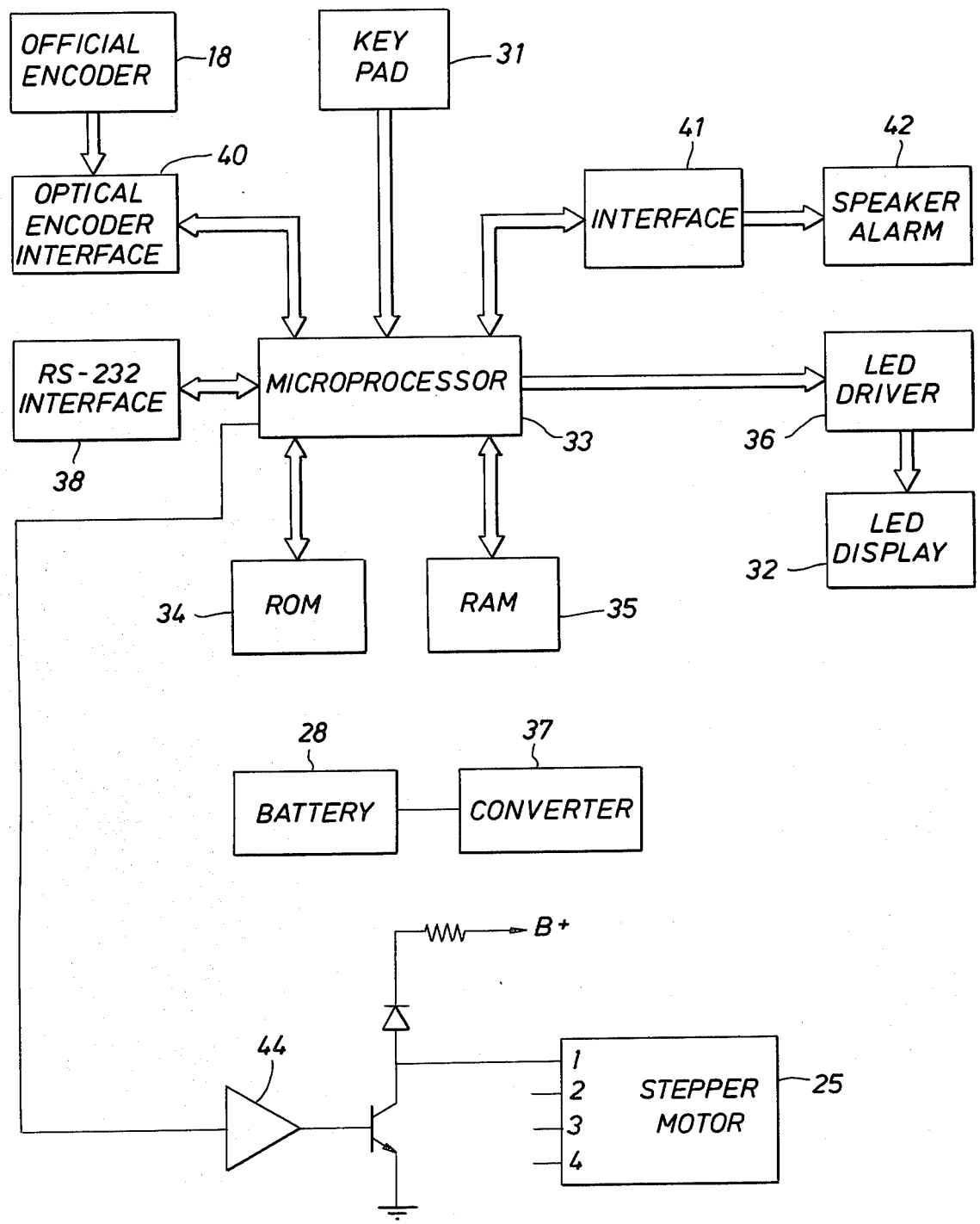
FIG. 2 is a schematic of the microprocessor control system incorporated with the apparatus of FIG. 1.

Attention is next directed to FIG. 2 of the drawings calibration switches are included at 33 to input set values which shows the circuitry of the present apparatus in greater detail. There, the key pad 31 forms input signals for switching the equipment on which signals are provided to a microprocessor identified by the numeral 33. It is connected to a ROM 34 and RAM 35. They store instructions for the operation of the apparatus. They also store data as it is measured dynamically, and at the conclusion of each test, the data is presented for output at the LED display 32. The latter is accomplished by forming the output data which is then provided to a LED display interface circuit 36. This incorporates display drivers.

The battery 28 is output to a converter 37. The converter forms various voltage levels required for operation of the equipment. The microprocessor is connected by means of a bus to an RS-232 interface circuit 38. This formats data for connection out or in through a hard copy printer or other input or output device. It provides a standard interface connection to enable such communication. The optical encoder 18 is connected to an optical encoder interface circuit. One model is the Hewlett-Packard HEDS-5000. This forms signals which are formatted from the interface 40 for the microprocessor 33. The interface 40 thus presents the data in a format suitable for use by the microprocessor.

Various alarm signals can be devised as will be discussed. These alarm signals are output from the microcomputer 33 to a beeper interface 41 which in turn is connected to a loud speaker 42 for sounding an audible alarm. As will be understood, visual alarms can also be output to the LED display 32.

The stepping motor 25 is powered by pulse amplifiers. In one brand, there are four motor terminals and four pulse amplifiers are utilized. An exemplary pulse amplifier is illustrated in FIG. 2 of the drawings. An inverter 44 is connected to a relatively large transistor 45. The transistor is switched between saturation and off to form a relatively square output wave on the conductor 46. Additional motor driver circuits are included; the several motor drivers at 48 are preferably identical to the circuit included in FIG. 2. They provide pulses to the motor 25 for its rotation. The motor is mechanically connected as shown in FIG. 1 to rotate the sleeve 20.

Figure 3:
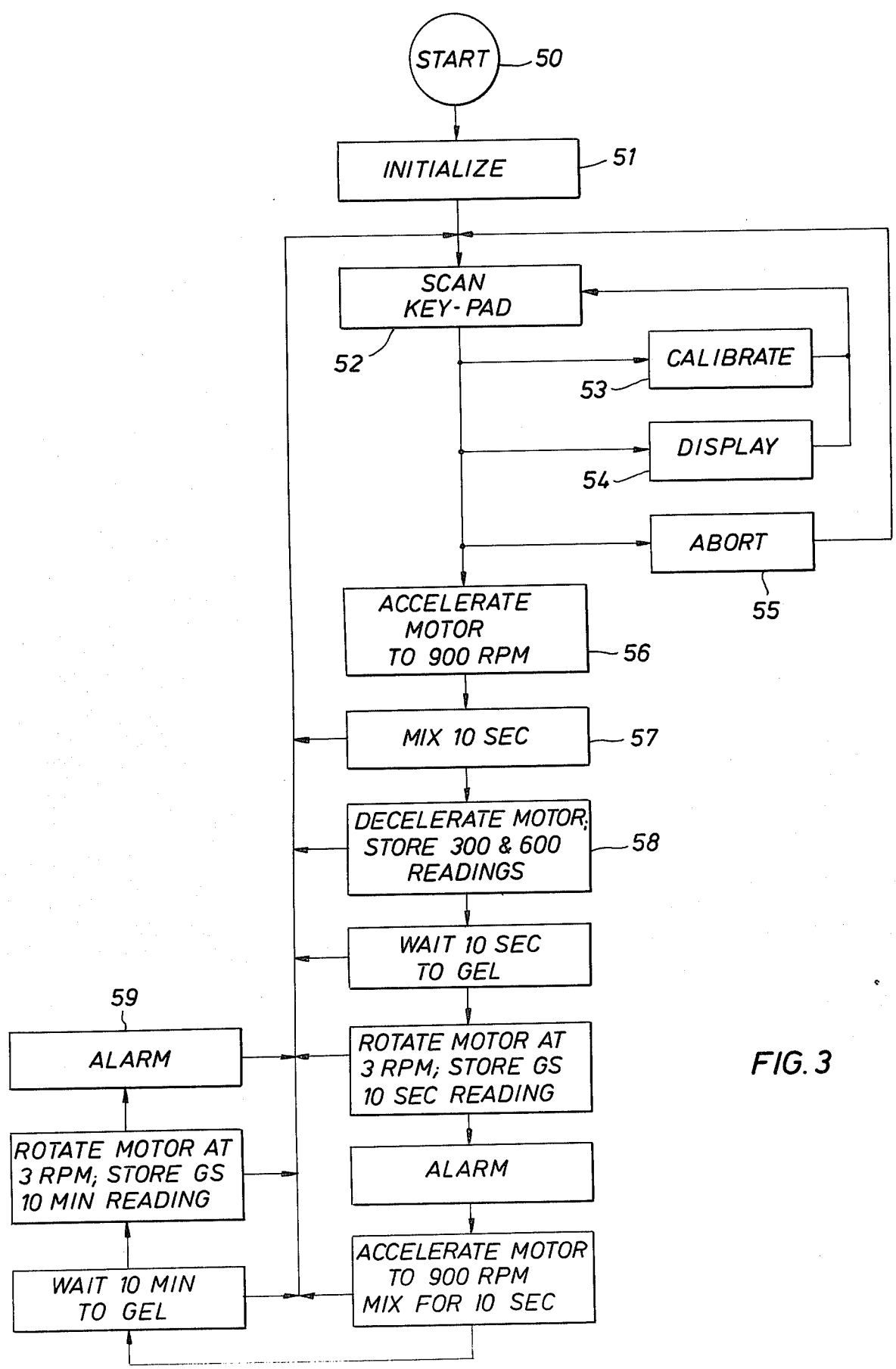
FIG. 3 is a flowchart of instructions to be stored in memory for implementation through the microprocessor to operate the viscosity measuring apparatus of the present disclosure to carry out a programmed test routine.

Attention is next directed to FIG. 3 which is a flow chart of instructions for carrying out a test program. The test program includes the following sequence of instructions which are conformed to API test standards currently in effect for fluid used in drilling oil wells. As will be appreciated, the test routine can be changed, as for example, changing the specified RPM or waiting periods. Accordingly, the measurements given in FIG. 3 are representative of one routine and can be modified as required. The sequence or programs is entered at 50 by the first step which is the starting step. The first entry is to obtain scale values including parameters. The next step is initialize at 51. This is input either through stored values or through values which are entered through the key pad. The key pad is scanned at the next step which is identified at 52. These values are then input to the calibration step 53. One or more calibration values is input at 53 through calibration, and the calibration value is incorporated to thereby calibrate the entire system. Further, there is a display sequence at 54 which displays various data, the termination of steps and the measured data. The data and vents are preferably labelled so that they will be recognized, not ambiguous, and in a suitable dimension for direct use. For instance, time intervals should be measured in seconds, and velocity should be measured in RPM. Accordingly, the display stores the instructions for outputting the correct measurements on the data and further signifying the completion of various steps. The program further includes an abort instruction 55 which resets the program to the beginning step.

Several steps are shown at 56 and following. The steps are specified and are in sequence. This sequence can be modified as required. However, to carry out the steps, the first step 56 is the operation of ramping the motor up to 900 RPM. The motor is ramped over a specified time interval to 900 RPM. Utilizing a stepping motor which operates at 200 steps per revolution, this is a modest speed of 3000 pulses per second which can be readily accommodated by the stepping motor. There is a smoothing action which is achieved as the motor speeds up. The smoothing action results in a smooth transition of the rotatable sleeve from the initial position (non-moving) to the ultimate speed of 900 RPM. This is accomplished in a specified interval, again a scale factor which can be designated by the operator. For instance, it is suitable to step the motor up to full speed of 900 RPM over a period of about 300 seconds.

Using the representative steps shown in FIG. 3, the first step is ramping the motor to speed at step 56 and then holding that speed steady for ten seconds, this being being step 57. The next step is step 58 which involves ramping the motor to a lower speed. It will be observed that steps 57 and 58 required readings to be taken and stored. The steps continue through the routine shown in FIG. 3. Eventually, the last step is reached which is the end of test which is identified at step 59. The end of test sounds an alarm. This indicates to the operator that the full routine has been finished.

Along the procedure, various readings are taken and stored. The readings which are stored are obtained from the rotatable bob, and these readings are deflection from the reference azimuth. These readings are optically encoded by the encoder 18 and are put into a format suitable for storage in memory. The readings that are stored are then used as a means of calculating various measurements obtained through the use of the equipment. Consider the following examples. A first viscosity data obtaining the deflection of the bob (an angular measurement) at 600 RPM. A second viscosity data is obtained by storing the deflection at 300 RPM. These data assist in deriving the plastic viscosity, normally expressed in units known as centipoises. The yield point of the drilling fluid can also be derived. That is normally related to the readings obtained at 300 RPM. The Newtonian viscosity is normally obtained at 300 RPM. The apparent viscosity at 600 RPM in centipoises is the angular deflection obtained at 600 RPM. The apparent viscosity at 300 RPM is the angular displacement at 300 RPM. All of these data require scale factors for conversion. Such scale factors are easily implemented by stored conversion factors from memory. The yield point is the difference between the 300 RPM apparent viscosity and the plastic viscosity. The plastic viscosity is the difference in the 600 and 300 RPM apparent viscosities.

The gel strength of the fluid is obtained by thoroughly mixing the fluid at 900 RPM for a specified interval and then permitting ten seconds of rest. Then, operating at a speed of 3 RPM, the maximum or peak deflection of the shaft is the initial gel strength in pounds per 100 square feet readily measured by the optical encoder.

This apparatus has the advantage that operator skills are minimal. No dials or gages are read; no calculations are required in the field. Rather, the output values including parameters of the drilling fluid such as viscosity, apparent viscosity, yield point, gel strength after different intervals are all output by the LED display.

While the foregoing is directed to the preferred embodiment, the scope is determined by the claims which follow.

What is claimed is:

1. An automatic programmable viscometer comprising:
   (a) a base for supporting a container with drilling fluid therein;
   (b) a rotatable tubular sleeve extending into the container on said base for engaging drilling fluid therein;
   (c) pulse operated stepper motor drive means for rotating said sleeve;
   (d) a cylindrical bob concentrically positioned within said tubular sleeve and adapted to be placed in drilling fluid in a container, said bob connected with a rotatable bob shaft extending thereabove;
   (e) rotational encoding means connected to said shaft for forming an indication of rotation thereof conveyed thereto by said bob;
   (f) programmable drive control means connected with said pulse operated stepper motor drive means for controlling rotation of said tubular sleeve in a specified sequence to carry out a test program of drilling fluid wherein measurements from said encoding means are recorded dynamically during the test program;
   (g) input means responsive to externally generated signals for inputting commands to said drive control means; and
   (h) output means for indicating fluid measurements related to the viscosity of the drilling fluid in the container.

2. The apparatus of claim 1 wherein said programmable drive control means includes memory means having a stored sequence of instructions therein and microprocessor means connected to said memory means for sequentially forming control signals for said drive means.

3. The apparatus of claim 2 wherein said pulse operated motor has input pulse amplifiers for driving said motor.

4. The apparatus of claim 3 wherein said pulse amplifiers are connected to said microprocessor means.

5. The apparatus of claim 1 wherein said rotatable sleeve has a driven pulley;
 (a) said drive means has a driver pulley;
 (b) a yieldable belt engaging both of said pulleys to rotate said rotatable sleeve; and
 (c) wherein said belt yields sufficiently and wherein said pulleys have sufficient inertia during rotation to jointly smooth rotation of said sleeve driven by said pulsed operated stepper motor drive means.

6. The apparatus of claim 5 including a support platform positioning said drive means and said driver pulley in a fixed and raised location, and said driven pulley is in a common plane to said driver pulley; and said driven pulley is journalled to said sleeve above said platform.

7. The apparatus of claim 1 including a key pad operable to input data for operation;
 (a) memory means;
 (b) microprocessor means connected to said memory means and said key pad;
 (c) alarm output means;
 (d) alarm output driver means connected between said alarm output means and said microprocessor means for forming alarm outputs as determined by said microprocessor means;
 (e) wherein said output means comprises a visual display of designated symbols; and
 (f) wherein a sequence of scaled and designated instructions in memory operate said pulsed operated stepper motor drive means to test drilling fluid, and as said bob rotates said shaft enabling dynamic measurement of said rotational encoding means to obtain meansurements preliminary to viscosity data.

8. The apparatus of claim 7 wherein plastic viscosity is proportional to the difference in angular deflection of said bob at higher and lower speeds.

9. The apparatus of claim 8 wherein said speeds are 600 and 300 RPM.

10. The apparatus of claim 7 wherein Newtonian viscosity is proportional to the angular deflection of said bob at a selected speed.

11. The apparatus of claim 10 wherein the speed is 300 RPM.

12. The apparatus of claim 7 wherein the apparent viscosity is proportional to the angular deflection of said bob at a selected speed.

13. The apparatus of claim 12 wherein the speed is 600 RPM.

14. The apparatus of claim 7 wherein said memory means stores instructions for operation of said drive means for timed durations at specified velocities;
 (a) wherein said encoder means forms encoded measurements of shaft angular deflection from rotation of said bob, said encoder measurements being stored in said memory means for specified speeds of said drive means in a predetermined sequence, said encoded measurements in said memory means being convertable into viscosity data of the drilling fluid.

15. The apparatus of claim 14 wherein said encoded measurements are formatted and converted by scale factors into viscosity data.

16. The apparatus of claim 15 including a visual display for indicating viscosity data from said encoded measurements.

17. The apparatus of claim 16 including a visual display driver means connected to said microprocessor means.

* * * * *